(12) United States Patent
Forbes

(10) Patent No.: US 7,488,798 B2
(45) Date of Patent: Feb. 10, 2009

(54) ALTERED INSULIN-LIKE GROWTH FACTOR BINDING PROTEINS

(75) Inventor: Briony Forbes, Adelaide (AU)

(73) Assignee: University of Adelaide, Adelaide (AU)

( * ) Notice: Subject to any disclaimer, the term of this patent is extended or adjusted under 35 U.S.C. 154(b) by 0 days.

(21) Appl. No.: 10/519,890

(22) PCT Filed: Jul. 11, 2003

(86) PCT No.: PCT/AU03/00898

§ 371 (c)(1), (2), (4) Date: Dec. 29, 2004

(87) PCT Pub. No.: WO2004/007543

PCT Pub. Date: Jan. 22, 2004

(65) Prior Publication Data

US 2006/0153853 A1  Jul. 13, 2006

(30) Foreign Application Priority Data

Jul. 12, 2002 (AU) .............................. 2002950188

(51) Int. Cl.
*C07K 14/00* (2006.01)
*C07K 14/65* (2006.01)
*C07H 21/00* (2006.01)

(52) U.S. Cl. ..................................... 530/350; 536/23.1

(58) Field of Classification Search ........................ None
See application file for complete search history.

(56) References Cited

U.S. PATENT DOCUMENTS 7,071,160 B2 * 7/2006 Yamano et al. ................. 514/2

OTHER PUBLICATIONS

Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12: 425-427.*
Richardson et al. 2003. Virchows Arch. 442: 329-335.*
Ngo et al., 1994, The Protein Folding Problem and Tetiary Structure Prediction, pp. 492-495.*
Skolnick et al., 2000, Trends in Biotech. 18(1):34-39.*
Bork et al., 1996, Trends in Genetics 12:425-427.*
Eiseman et al., Clin Cancer Res. 2007; 13: 2121-2127.*
Rajaram et al., Endocr Rev 1997;18: 801-31.*
Boulle et al. J Clin Endocrinol Metab 1998; 83: 1713-20.*
Moore et al. Int J Cancer. 2003: 105: 14-19.*
Kibbey et al. Mol Pharmacol 2006;69: 833-45.*
elmhurst.edu/~chm/vchembook/561aminostructure.html; downloaded on Feb. 15, 2008 at 3:55:54pm; 3 pages.*
Imai, Y. et al., "Protease-resistance form of insulin-like growth factor-binding protein 5 is an inhibitor of insulin-like growth factor-1 actions on porcine smooth muscle cells in culture.", Journal of Clinical Investigation, vol. 100, No. 10, 1997, pp. 2596-2605.
Lucic, M. et al., "Secretion in *Escherichia coli* and phage display of recombinant insulin-like growth factor binding protein-2.", Journal of Biotechnology, vol. 61, 1998, pp. 95-108.
Clemmons, David R.; "Use of mutagenesis to probe IGF-binding protein structure/function relationships"; Endocrine Reviews (2001), vol. 22 (6); pp. 800-817.
Qin Xuezhong et al.; "Studies on the role of human insulin-like growth factor-II (IGF-II)-dependent IGF binding protein (hIGFBP)-4 protease in human osteoblasts using protease-resistant IGBP-4 analogs"; Journal of Bone and Mineral Research (1999), vol. 14(12), pp. 2079-2088.
Miyakoshi, Naohisa et al.; Systemic administration of insulin-like growth factor (IGF)-binding protein-4 (IGFBP-4) increases bone formation parameters in mice by increasing IGF bioavailability via an IGFBP-4 protease-dependent mechanism; Endocrinology (2001); vol. 142(6); pp. 2641-2648.
Canover, C. A. et al.; Cleavage analysis of insulin-like growth-factor (IGF) dependent IGF-binding protein-4 proteolysis and expression of protease-resistant IGF-binding protein-4 mutants; Journal of Biological Chemistry, American Society of Biolochemical Biologist, Birmingham, US (1995); vol., 270 (9), pp. 4395-4400.
Clemmons, D. et al.; "Role of insulin-like growth factor binding protein in the control of IGF actions"; Progress of Growth Factor Research; vol. 6, No. 2-4; 1995; pp. 357-366.
Bramani, S. et al.; "Amino acids within the extracellular matrix (ECM) binding region (201-218) of rat insulin-like growth factor binding protein (IGFBP)-5 are important determinants in binding IGF-I"; Journal of Molecular Endocrinology; vol. 23, 1999, pp. 117-123.

* cited by examiner

*Primary Examiner*—Elizabeth C. Kemmerer
*Assistant Examiner*—Christina Borgeest
(74) *Attorney, Agent, or Firm*—Foley & Lardner LLP

(57) ABSTRACT

Altered IGFBPs are able to bind IGF, but the release is inhibited by resistance to protease cleavage and/or reduced binding to extracellular matrix (ECM). Alterations have been made in IGFBP-2 to the linker domain in particular and to two amino acid motifs found to be important for ECM binding. IGF-1 mediated proliferation of cancer cells have been inhibited by use of the altered IGFBPs.

24 Claims, 6 Drawing Sheets

ALTERED INSULIN-LIKE GROWTH FACTOR BINDING PROTEINS

FIELD OF THE INVENTION

This invention relates to an altered Insulin-like Growth Factor Binding Protein (IGFBP) with reduced IGF (Insulin-like Growth Factor) release characteristics. The IGFBP of the invention is proposed to be useful for therapeutic purposes, such as treatment of certain cancers. A specific form of the invention relates to an altered IGFBP-2.

BACKGROUND TO THE INVENTION

Insulin-like growth factors (IGF-I and IGF-II) are small, highly-related proteins (~7.5 kilodaltons) which mediate anabolic, mitogenic and anti-apoptotic activities in a wide variety of cell types. These actions result from IGF interaction with and subsequent activation of the type 1 IGF receptor (IGF1R) (Sepp-Lorenzino, (1998), Baserga, 1999). A second unrelated receptor (the type 2 IGF receptor or IGF2R) has the major function of regulation of IGF-II levels by internalisation and degradation (Wang et al., 1994) and current evidence suggests that the IGF2R acts as a tumour suppressor of IGF-II-dependent tumours (Braulke, 1999).

IGFs are produced by the liver, providing circulating IGF, and are also secreted locally in most tissues. A family of 6 high-affinity IGF binding proteins (IGFBP-1 to -6) act to increase the half-life of IGFs in circulation (predominantly as the IGFBP-3·ALS·IGF complex) and also to transport IGFs to target tissues. Within target tissues IGFBPs can either enhance or inhibit IGF action. IGFBPs can inhibit the interaction of IGF by blocking binding to the IGF1R. However, under certain circumstances IGFBPs can release IGF, thereby making IGF available for binding to the IGF1R. This results in an enhancing effect on IGF action. Release mechanisms include 1) proteolysis of the IGFBPs and 2) IGFBP binding to the extracellular matrix (ECM), both of which lower their affinity for IGF. Extracellular matrix binding is also believed to assist the localisation of IGF close to the cell surface and therefore near IGF1Rs. The outcome of IGFBP action is controlled by a balance between local proteolytic activity and the binding of IGFBPs to the ECM.

Substantial evidence (in vivo and in vitro) implicates insulin-like growth factors (IGFs) and IGF binding proteins (IGFBPs) in cancer. Many tumour cells (including prostate and breast) secrete more IGF-II and IGFBP-2 than their normal counterparts and their serum levels commonly rise as cancers progress (Cohen et al., (1994); Thrasher et al., (1996); Ho et al., (1997); Chan et al., 1998). IGF secreted by tumour cells binds to the Type 1 IGF receptor potentiating tumourigenesis and metastasis (DiGiovanni et al., 2000).

The proteolysis of IGFBP-2 has been detected under a number of normal and abnormal physiological conditions. For example, IGFBP-2 fragments have been detected in human milk and cleavage occurred predominantly in the linker region between the N- and C-domains and including sites at residues 168 and 180/181 of hIGFBP-2 (Ho and Baxter, 1997; Elminger et al., 1999). Proteolysed IGFBP-2 is also found in serum during pregnancy. IGFBP-2 is also cleaved by proteases produced by cancer cells (Michell et al., 1997). The specific cancer cell proteases have not been well characterised although Cathepsin D produced in vitro by prostate epithelial cells has been shown to degrade IGFBP-2 (Kanety et al., 1993; Nunn et al., 1997). Preferential proteolysis of IGFBP-2 has been demonstrated in colonic cancers (Michell et al., 1997) and neuroblastoma cells (Menouny et al., 1997). Specific cleavage sites have not been described for proteolytic products generated by cancer proteases.

Protease cleavage sites have been identified in the IGFBP-3, -4 and -5 sequences. Proteolysis is generally within the linker regions of these proteins although it can be in the C-domain. Protease resistant IGFBP-4 and IGFBP-5 (Imai et al., 1997) have been generated by mutating specific residues at cleavage sites or by deletion of some linker region residues (deletion of 121-141 of IGFBP-4 rendered it resistant to a protease in pregnancy serum (Byun et al., 2000).

IGFBP-2 binds to human fibroblast extracellular membrane preparations (Arai et al., 1996) and glycosaminoglycans (Russo et al 1997, Arai et al., 1996). There are 2 potential matrix binding sites within the IGFBP-2 sequence. Current evidence suggests that the basic region of hIGFBP-2 (residues 227-244), corresponding to residues 201-218 of hIGFBP-5, may act as a site for matrix binding (Arai et al., 1996). Using a synthetic peptide based on residues 201-218 of hIGFBP-5 (residues known to be important for matrix binding) Arai et al., 1996, inhibited IGFBP-2 binding to heparin-Sepharose. Hodgkinson et al., (1994) predicted a glycosaminoglycan (GAG) binding site in IGFBP-2 based on a short GAG-binding consensus sequence described by Cardin and Weintraub (1989). This XBBXBX (B=basic, X=undefined) motif at residues 179-184 of hIGFBP-2 lies in the central domain. There is no published evidence that this motif plays a role in GAG binding.

For the purposes of this specification the word "comprising" means "including but not limited to", and the word "comprises" has a corresponding meaning. Also a reference within this specification to a document is not to be taken as an admission that the disclosure therein constitutes common general knowledge in Australia.

SUMMARY OF THE INVENTION

This invention arises from the alteration of IGFBP-2 in a manner that inhibits the release of IGF-I and IGF-II. The inhibition of release results from the introduction of changes to the IGFBP-2 resulting in reduced binding to extracellular matrix (ECM) and reduced susceptibility to proteolysis by one or more proteases. This altered IGFBP-2 is proposed to be useful for its ability to inhibit growth of IGF-dependent tumours such as colon, prostate and breast cancers. This is to the inventor's knowledge the first time that an altered IGFBP has been constructed to contain both reduced ECM binding and reduced proteolytic susceptibility and the first time that this combination has been shown to be effective at inhibiting the release of IGF-I and IGF-II. It is proposed that this approach will be effective not only for IGFBP-2 but also for other IGFBPs. Additionally this is to the inventor's knowledge the first time that there have been functional data to show the location of the two ECM binding sites for IGFBP-2, and a demonstration that these together with alteration of proteolysis sites result in inhibition of the release of IGF-I and IGF-II. Additionally this is the first time to the inventor's knowledge that an overlapping IGF and ECM binding site has been altered in a manner that still allows IGF binding but not ECM binding.

The invention might in a first broad aspect be said therefore to reside in an altered IGFBP-2 molecule able to effect binding of IGF-I or IGF-II with high affinity characterised in an inhibited release of IGF on contact with extracellular matrix or exposure to a protease.

In a second form of the first aspect of the invention might be said to reside in an altered IGFBP molecule able to effect binding of IGF-I or IGF-II with high affinity characterised in an inhibited release of IGF on contact with extracellular matrix and exposure to a protease.

Cleaved IGFBP-2 has greater than 10 fold weaker affinity for IGF (Carrick, 2001). It is desirable for the altered IGFBP-2 to have at least to have an affinity for IGF-I equivalent to the IGF type 1 receptor which is 10 fold lower than that of native IGFBP-2 for IGF-I. This allows effective competition with the receptor for IGF binding and the term high affinity binding of IGF should be understood in that context.

Regions required for IGF binding have not been fully elucidated however considerable effort has been made to define these regions. Thus for example we (Hobba et al., 1998) and others (Zeslawski et al., 2001) have identified residues in the distal part of the N-domain involved in IGF binding. Similarly, the minimum C-domain length of IGFBP-2 required for IGF binding has been described (Forbes et al., 1998). WO 00/23469 also describes the IGF binding domain which document is incorporated herein in its entirety by reference. Methods for assaying IGF binding are known in the art and can be readily employed to ascertain whether the altered IGFBP is able to bind IGF or not.

The inventor has identified two ECM sites for IGFBP-2 and shown that mutations in these lead to reduced heparin binding. The first ECM site for IGFBP-2 spans sequence 179-184 and consists of the sequence PKKLRP [SEQ ID No 1] and was originally proposed on the basis of homology with the consensus sequence for matrix binding proteins (namely XBBXBX, Hodgkinson et al., 1994). The second ECM binding sequence of IGFBP-2 identified is at 227-244 by homology with IGFBP-3 and IGFBP-5 and consists of sequence KHGLYNLKQCKMSLNGQR [SEQ ID No 2]. Suitable reference sequence is available from sequence databases. Thus the nucleotide sequence of cDNA of human IGFBP-2 might be accessed from the NCBI sequence database as accession number NM000597. Suitable amino acid sequence predictions can be made from the nucleotide sequence.

The invention might also in a third form of the first aspect be said to reside in an altered IGFBP-2 molecule able to effect binding of IGF-I or IGF-II with high affinity said IGFBP-2 molecule having alterations in any one or more amino acids in both ECM binding sites, a first ECM binding site being located at sequence 179 to 185 and a second ECM binding site being located at sequences 227 through 244, the alterations separately and together inhibiting the binding of the IGFBP-2 to ECM.

Preferably residues between 227 and 236 are substitution mutations because it is thought that at least part of this site may also be important for IGF binding. Whereas the 179-185 alteration may be achieved by deletion, inversion, substitution or other gross alteration, however preferably this is altered by amino acid substitution.

Generally substitution of a basic amino acid for an amino acid of different character, that is either neutral, or acidic is found generally to have a disrupting effect on matrix binding motifs.

It is found by the inventor that utilising the mutations so far introduced into IGFBP-2 that alteration of one of the two ECM sites alone is not sufficient to totally abolish ECM binding. Whilst the present invention preferably provides for the alteration of both ECM sites, the invention might also encompass the provision of alteration in one only of the ECM binding sites, and perhaps in combination with an altered protease cleavage and/or binding site.

Set out below are sequences shown or proposed to be the ECM binding sites for all six IGFBPs.

ECM binding sites (in the C-domain between the 14$^{th}$ and 16$^{th}$ cysteine residues)

| | | |
|---|---|---|
| IGFBP-3 | CDKKGFY<u>KKK</u>Q<u>C</u>RPS<u>KGRKR</u>GFC (Firth, 1998) | [SEQ ID No 3] |
| IGFBP-5 | CD<u>RK</u>GFY<u>KRK</u>QC<u>K</u>PS<u>RGRKR</u>GIC (Arai, 1996b) | [SEQ ID No 4] |
| IGFBP-2 | CDKHGLYNLKQCKMSLNGQRGEC<br>    *     * *      * | [SEQ ID No 5] |
| IGFBP1 | CNKNGFYHSRQCETSMDGEAGLC | [SEQ ID No 6] |
| IGFBP4 | CDRNGNFHPKQCHPALDGQRGKC | [SEQ ID No 7] |
| IGFBP6 | CDHRGFYRKRQCRSSQGQRRGPC | [SEQ ID No 8] |

*= conserved positively charged residues

Sites for IGFBP 3 and IGFBP 5 have been published previously the present data establishes the binding site for IGFBP-2 and the sites for IGFBP1, 4, and 6 are suggested by reason of amino acid alignment.

The invention might also encompass an altered IGFBP-1, -4, or -6 having an alteration in the ECM binding sites.

Alternatively in this first aspect of the invention it might be that a satisfactory decreased release of IGF is achieved solely by inhibition of ECM binding by amino acid substitution at the second ECM binding site. Such decreased release might be the result of the close association between the IGF binding site and the second ECM binding site, and therefore the first aspect of the invention might reside in an altered IGFBP molecule and perhaps preferably an IGFBP-2 molecule that has one or more amino acid substitutions in the ECM binding site that still allows binding of IGF, whilst still inhibiting binding of ECM and thereby also inhibiting IGF release.

It is thought that the positively charged residues are important for binding and thus substitution of these are likely to result in inhibition of binding. The substitution might be a non conservative substitution such as the following alanine (A) substitutions for lysine (K).

| Site 1 | Site 2 |
|---|---|
| PKKLRP [SEQ ID No 9] | KHGLYNLKQCKMSLNGQR [SEQ ID No 14] |
| PAKLRP [SEQ ID No 10] | AHGLYNLKQCKMSLNGQR [SEQ ID No 15] |
| PKALRP [SEQ ID No 11] | KHGLYNLAQCKMSLNGQR [SEQ ID No 16] |
| PKKLAP [SEQ ID No 12] | KHGLYNLKQCAMSLNGQR [SEQ ID No 17] |
| PAALAP [SEQ ID No 13] | AHGLYNLAQCAMSLNGQR [SEQ ID No 18] |

Substitutions of the lysine residues by other amino acids might also be contemplated.

The altered IGFBP-2 of the first aspect of the invention preferrably also has an alteration at any one or more proteolytic cleavage sites whereby to inhibit the release of an IGF when subjected to a protease specific for the proteolytic cleavage site.

A preferred form of the first aspect of the invention comprises substitution mutations at the first and second ECM binding sites, perhaps those referred to above, together with any one or more deletions in the linker domain that remove one or more proteolytic cleavage sites.

As indicated above in certain aspects the invention encompasses alterations that inhibit IGF release on exposure to one or more proteolytic enzymes. Many proteolytic enzymes to which IGFBPs are susceptible have as their target the linker domain. The proteolytic enzyme that the altered IGFBP is exposed to on delivery for therapeutic purposes may differ depending on the conditions to be treated. It is known that tumour cell lines vary in the proteolytic enzymes they produce. It has been shown by the inventor that a substantial deletion in the linker domain of IGFBP-2 leads to resistance to proteolytic cleavage whilst at the same time maintaining protein stability and maintaining IGF binding at high affinity. A preferred alteration of the IGFBP that leads to protease resistance is therefore one or more deletions within the linker domain. The size of the deletion or deletions may be varied. It has been found by the inventor that a deletion of substantially all of the linker region still led to IGF binding. With a deletion of substantially all of the linker domain it is preferred that amino acids from about 180 through to 191 are maintained.

Smaller deletions may also be suitable for removal of sites that make the IGFBP susceptible to proteolysis, thus deletions of amino acids about 110 through to about 170 has resulted in a decrease susceptibility to proteolysis.

Resistance to proteolysis may also be achieved by more targetted alteration to sites important for proteolytic cleavage or binding.

Substitution of residues other than those involved in proteolysis or ECM binding might also be contemplated, and these might be conservative substitutions or non-conservative substitutions, deletions, duplications, inversions and other rearrangements, provided that the altered IGFBP is still capable of high affinity IGF binding. Additionally the altered IGFBP might have additional changes such as glycosylations or other chemical modifications.

The proteins may be a fusion protein which assists in the purification, thus the protein may include a C terminal 6 histidine tag which provides for nickel affinity purification. Other fusion purification systems are also known and may be used. For bacterial systems a fusion protein may include a signal sequence, such as one derived from ompA, adapted to have the protein secreted through the surface of the cell.

In a second aspect the invention might be said to reside in a nucleic acid encoding one or more of the proteins or amino acid sequences of the first aspect of the invention. In a preferred form the nucleic acid is carried by a vector, the vector having nucleic acid operably linked with a control sequence including a promoter for transcription leading to expression of the protein or amino acid. Any one of the very many known vectors for that purpose may be used. Alternatively the vector may be used simply to introduce the nucleic acid encoding the altered IGFBP into a host cell for integration into a chromosome host cell, and might therefore be a retroviral expression vector.

In a third form the invention might be said to reside in a recombinant cell carrying a vector or the nucleic acid of the second aspect of the invention. The host cell might be intended for expression of the altered IGFBP which can thus be produced and purified such that the purified protein may be then separately used or administered as desired. The host cell might be bacterial, yeast, plant or mammalian. Alternatively the host cell may be intended for introduction into a treated animal such as a human for gene therapy purposes.

In a fourth form the invention might be said to reside in a pharmaceutical composition. The composition including the altered IGFBP-2 of the first aspect of the invention as an active component. The pharmaceutical composition may be formulated in accordance with an approved method, and may include a carrier which may or may not be fused to the altered IGFBP, or conjugated with the altered IGFBP. The composition may additionally include other medicinal agents, pharmaceutical agents, adjuvants, diluent, excipients and the like.

The invention might in a fifth form also be said to reside in a method for decreasing serum and/or tissue levels of biologically active IGF-I or IGF-II by administering to a mammal an amount of altered IGFBP of the first aspect of this invention effective to inhibit the release of IGF-I or IGF-II from the altered IGFBP and thereby decrease serum and tissue levels of biologically active IGF-I or IGF-II.

The fifth aspect of the invention contemplates the expression of exogenous nucleic acid encoding the altered IGFBP-2 in one or more cells of the animal of human patient, as a so called gene therapy approach.

Generally, gene therapy is used to increase (or overexpress) altered IGFBP-2 levels in the mammal. Nucleic acids which encode IGFBP-2 be used for this purpose. Several nucleic acid molecules may be generated using the degeneracy of the genetic code that encodes the desired amino acid sequence.

There are two principal approaches to getting the nucleic acid (optionally contained in a vector) into the patient's cells for purposes of gene therapy: in vivo and ex vivo. For in vivo delivery, the nucleic acid is injected directly into the patient, usually at the site where the viperine is required. Preferably this might be in the liver. For ex vivo treatment, the patient's cells are removed, the nucleic acid is introduced into these isolated cells and the modified cells are administered to the patient either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

In vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem., 262: 4429-4432 (1987); and Wagner et al., Proc. Natl. Acad. Sci. USA, 87: 3410-3414 (1990). For a review of known gene marking and gene therapy protocols, see Anderson et al., Science, 256: 808-813 (1992). See also WO 93/25673 and the references cited therein.

Alternatively purified altered IGFBP can be administered to the mammal in a suitable carrier the altered IGFBP may be administered orally parenterally, topically transdermally. It might be preferred to provide the altered IGFBP in slow release from. Determination of appropriate dosages and formulation may be achieve by one of ordinary skill in the art using only routine experimentation. See for example Remington's Pharmaceutical Sciences (Martin E. E. ed, latest edition), Mack Publishing Co, Easton Pa.

Further, included within the scope of the present invention is the co-administration of an altered IGFBP-2 together with a cytotoxic or anticancer agent. Such agents suitably include antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophasphamide, melphalan, biochoroethylnitrosurea, hydroxyurea), platinum agents (e.g. cisplatin, carboplatin, oxaliplatin, JM-216, CI-973), anthracyclines (e.g., doxrubicin, daunorubicin), antibiolitics (e.g., mitomycin, idarubicin, adriamycin, daunomycin), topoisomerase inhibitiors (e.g., etoposide, camptothecins) or any other antineoplastic agents. (estramustine phosphate, prednimustine).

It is anticipated that altered IGFBP-2 used in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses.

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, vaginal, and the like.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or move thereof. Other suitable pharmaceutically acceptable excipients are described in Remington's Pharmaceutical Sciences, Mack Pub. Co., N.J. (1991), which is incorporated herein by reference.

In a sixth aspect the invention might be said to reside in a method of reducing IGF mediated proliferation of a population of cancerous cell in the presence of IGF, by contacting the population of cells with an altered IGFBP according to this invention.

Conditions that might be amenable to treatment in this way include cancers that are IGF dependant and these may include certain cancers of the breast, prostate, colorectal, lung, thyroid, ovaries, and brain as well as in childhood leukaemias, glioblastomas, and neuroblastomas.

It is contemplated that treatment of say prostate cancer according to the present invention may not necessarily be used on its own but as an adjunct to other methods.

By way of a shorthand notation the following three and one letter abbreviations for amino acid residues are used in the specification as defined in Table 1.

Where a specific amino acid residue is referred to by its position in the polypeptide of an protein, the amino acid abbreviation is used with the residue number given in superscript (i.e. Xaan)

TABLE 1

| Amino Acid | Three-letter Abbreviation | One letter Abbreviation |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Human IGFBP-2 (at concentrations of 3.1, 6.25, 12.5, 25 and 50 nM) was allowed to associate with the Biosensor surface (70 resonance units of hIGFBP-2) for 300 s (from t=150 s) and then dissociated for 900 s. Real time binding is measured in response units. Kinetic studies were performed at a flow rate of 30 μl/min to minimize mass transfer effects. The IGF-I-coated biosensor surface was regenerated with 10 mM HCl between binding cycles. For each binding curve the response obtained using control surfaces (no protein coupled) was subtracted.

Figure 5A:
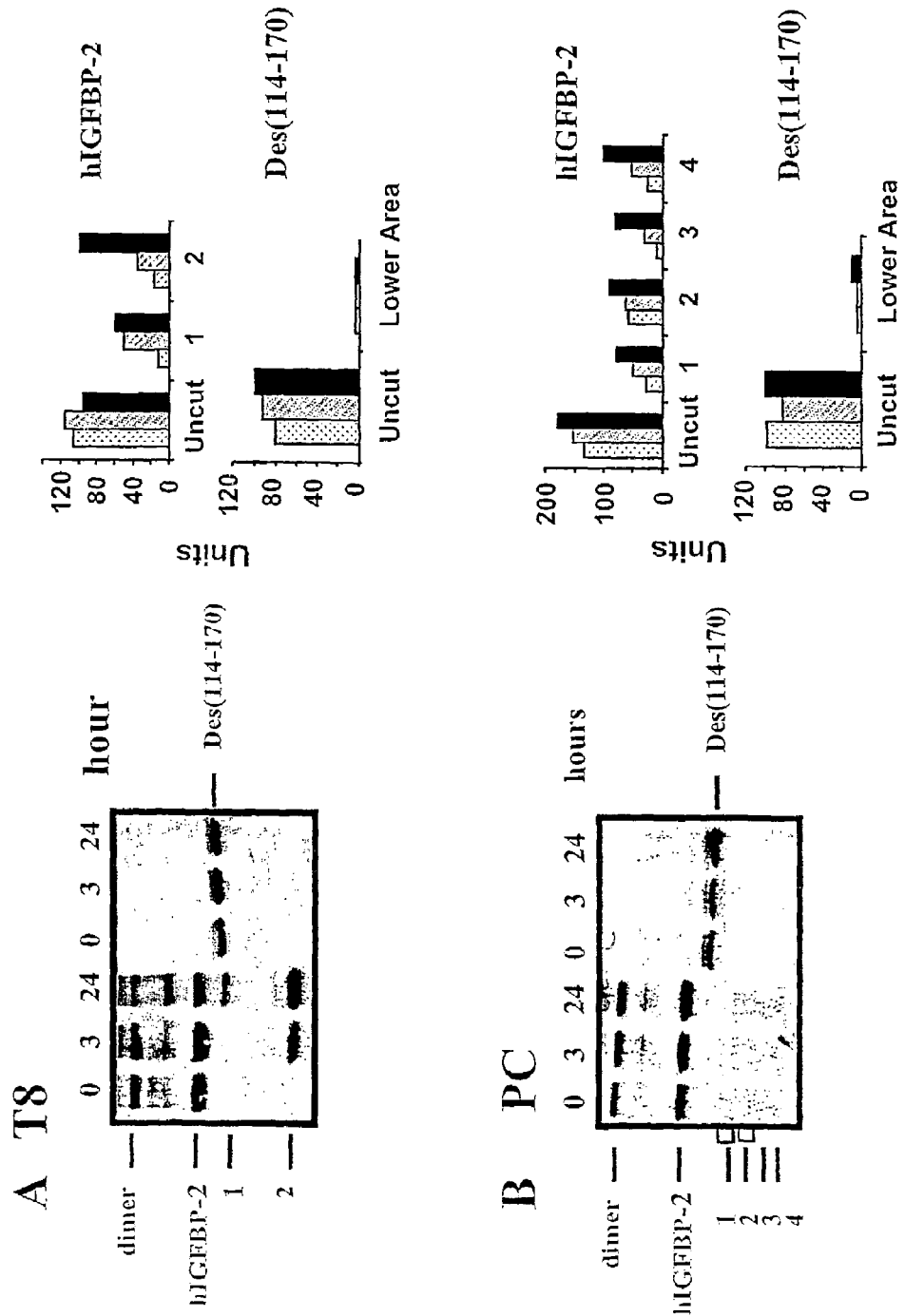

FIG. 5A Analysis of susceptibility of truncated hIGFBP-2 to proteolysis in culture media conditioned by cancer cells.

Truncated hIGFBP-2 and hIGFBP-2 were exposed to culture media of a) T84 colon cancer and b) PC3 prostate cancer for 0, 3 or 24 hours at 37 degrees. Samples were separated by SDS polyacrylamide gel electrophoresis on 10% tricine gels and transferred to nitrocellulose. hIGFBP-2 and cleavage products were detected with an anti-IGFBP-2 polyclonal antibody (left). hIGFBP-2 migrates at 34 kDa whereas Des (114-170)His migrates at 20 kDa. A dimer is present in hIGFBP-2 preparations. Proteolytic fragments range in size between 14 to 20 kDa. Densities of bands indicated on the blots were quantitated using the NIH image program and amounts of uncleaved or cleaved hIGFBP-2 graphed (right).

Figure 5B:
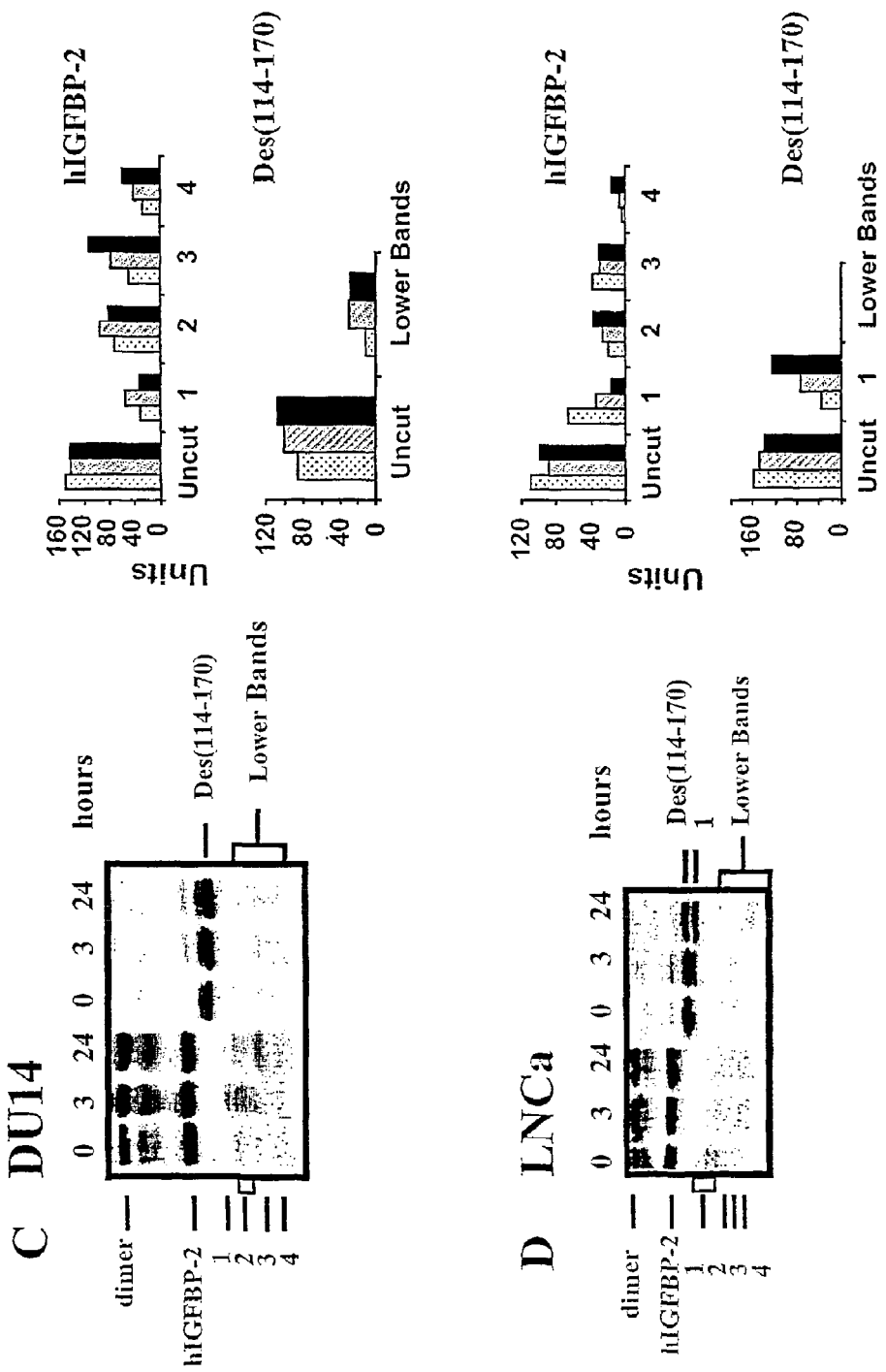
Figure 6:
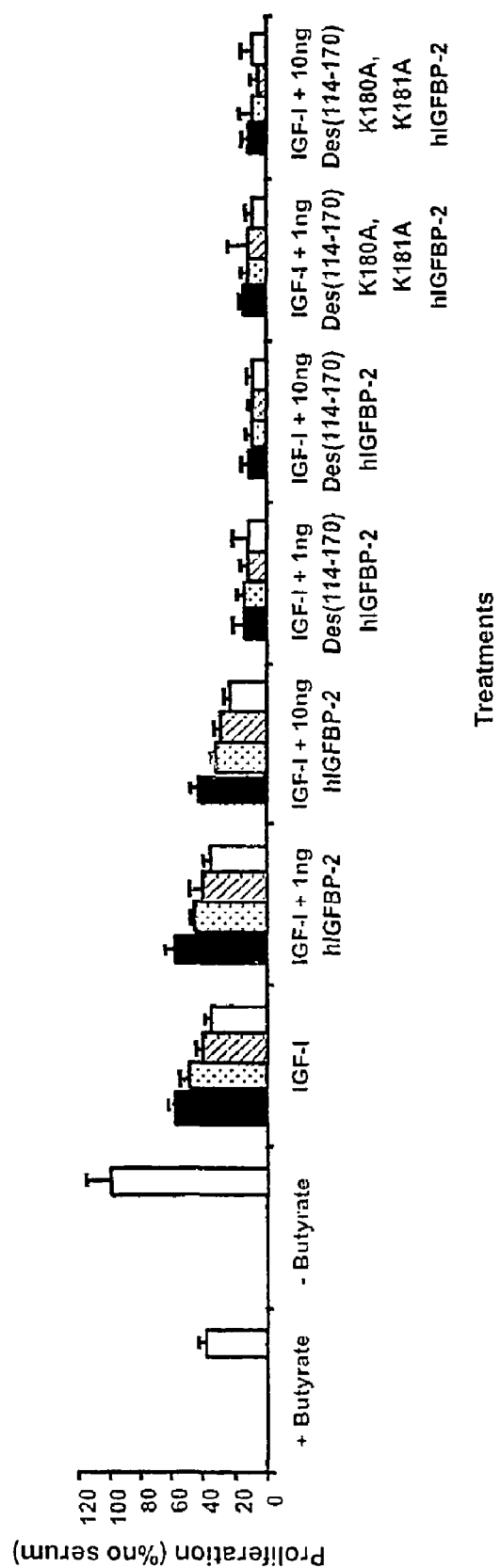

FIG. 5B Analysis of susceptibility of truncated hIGFBP-2 to proteolysis in culture media conditioned by cancer cells. Truncated hIGFBP-2 and hIGFBP-2 were exposed to culture media of c) DU145 and d) LNCaP prostate cancer cell lines for 0, 3 or 24 hours at 37 degrees. Samples were separated by SDS polyacrylamide gel electrophoresis on 10% tricine gels and transferred to nitrocellulose. hIGFBP-2 and cleavage products were detected with an anti-IGFBP-2 polyclonal antibody (left). hIGFBP-2 migrates at 34 kDa whereas Des (114-170)His migrates at 20 kDa. A dimer is present in hIGFBP-2 preparations. Proteolytic fragments range in size between 14 to 20 kDa. Densities of bands indicated on the blots were quantitated using the NIH image program and amounts of uncleaved or cleaved hIGFBP-2 graphed (right), and FIG. 6 Proliferation of HT-29 colorectal cells measured by Cell Titre Glo Assay (Promega). Apoptosis was induced with 5 mM butyrate and the ability of IGF-1 to promote cell survival was measured. Native IGFBP-2, DES(114-170) and DES (114-170) K180A K181A were added to cells treated with IGF-1 at various concentrations (0, 0.1, 0.3 and 0.65 nM) in the presence of butyrate. Results are expressed as a percentage of proliferation in the presence of culture medium alone. As Des (114-170) and Des (114-170) K180A K181A have two fold lower affinity for IGF-I and IGF-II respectively the percentage proliferation for these treatments was adjusted accordingly.

DETAILED DESCRIPTION OF THE INVENTION

Materials and Methods

Mutagenesis and Subcloning

Mutations of cDNA encoding hIGFBP-2 in the pBluescript vector (Stratagene, La Jolla, Calif., USA) were introduced using the Quikchange mutagenesis method (Stratagene). The following oligonucleotides were used to introduce the lysine (K) to alanine (A) mutations and the deletion mutant Des (114-170)His:

```
K180A K181AHis
Forward                              [SEQ ID No 19]
5' CTT GGC CTG GAG GAG CCT GCC GCC CTG CGA CCA CCC
CCT 3'

Reverse                              [SEQ ID No 20]
5' AGG GGG TGG TCG CAG GGC GGC AGG CTC CTC CAG GCC
AAG 3'

K227AHis
Forward                              [SEQ ID No 21]
5' ATC CCC AAC TGT GAC GCC CAT GGC CTG TAC ACC 3'

Reverse                              [SEQ ID No 22]
5' GGT GTA CAG GCC ATG GGC GTC ACA GTT GGG GAT 3'

K234AHis
Forward                              [SEQ ID No 23]
5' GGC CTG TAC AAC CTC GCC CAG TGC AAG ATG TCT 3'

Reverse                              [SEQ ID No 24]
5' AGA CAT CTT GCA CTG GGC GAG GTT GTA CAG GCC 3'

K237AHis
Forward                              [SEQ ID No 25]
5' AAC CTC AAA CAG GCC ATG TCT CTG AAC GGG 3'

Reverse                              [SEQ ID No 26]
5' CCC GTT CAG AGA CAT GGC GCA CTG TTT GAG GTT 3'

Des(114-170)His
Forward1                             [SEQ ID No 27]
5' GTT GCA GAC AAT GGC GCC GGC CAC TCA GAA GAA GCC
3'

Reverse1                             [SEQ ID No 28]
5' GCC TCC TTC TGA GTG GCC GGC GCC ATT GTC TGC AAC
3'

Forward2                             [SEQ ID No 29]
5' CGG CAC ATG GGC AAG GCC GGC AAG CAT CAC CTT 3'

Reverse2                             [SEQ ID No 30]
5' AAG GTG ATG CTT GCC GGC CTT GCC CAT GTG CCG 3'
```

The deletion mutant Des(114-170)His was generated by sequentially introducing two NaeI restriction sites in the cDNA encoding residues 114 and 170 respectively. The new clone was then digested with NaeI and religated to delete out the sequence between these sites.

Figure 1:
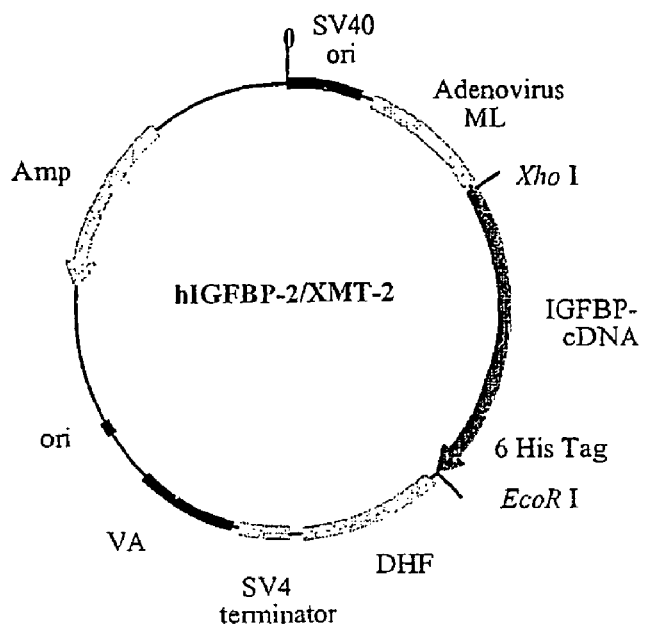
FIG. 1. Schematic diagram of the hIGFBP-2 expression vector constructed from the mammalian expression vector pXMT2 (Rathjen et al., (1990); Whyatt et al., (1993)). A colicin E1 origin of replication (ori) and the β-lactamase ampicillin resistance gene (Amp) enable selection and propagation in E. coli. Mammalian expression of the IGFBP-2 cDNA is driven by the adenovirus major late promoter (MLP). The dihydrofolate reductase (DHFR) gene is present for selection. A 6 Histidine tag is encoded at the 3' end of the IGFBP-2 cDNA sequence.

The cDNA clones encoding resultant mutant IGFBPs were transformed into DH5α E. coli. Clones were sequenced to confirm correct introduction of mutations. They were subsequently subcloned into the pXMT-2 vector using XhoI and EcoRI restriction sites and transformed into DH5α E. coli (see FIG. 1; Rathjen P. D. et al., (1990); Whyatt L. M. et al., (1993)). Mutant IGFBP-2 proteins were expressed upon transient transfection of COS-1 monkey kidney cells (ATCC: CRL 1650) with the mutant IGFBP-2 cDNAs. Cos-1 cells are cultured in DMEM (GIBCO)+10% FCS. The method of culture and purification is described in Forbes et al., (1998)

Purification and Analysis of Purity

Proteins were purified using standard Nickel affinity purification techniques taking advantage of a 6 histidine tag at the C-terminus of each protein. Purification is from culture medium as the IGFBP is secreted (Forbes et al, 1998). Following elusion from the nickel column, proteins were further purified using reverse phase high performance liquid chromatography (HPLC). Purity was analysed by rpHPLC, SDS PAGE and mass spectrometry. The mass of each mutant was determined by electrospray mass spectrometry (by Dr. Chris Bagley, Hanson Centre) and found to be correct (generally within the limits of the mass spec=1 mass unit/10,000 daltons).

Measurement of IGF Binding Affinities

IGF binding affinities of hIGFBP-2 and mutants were determined by surface plasmon resonance using the BIAcore with IGF-I or IGF-II coupled to the sensor surface (for details of method see Carrick et al., (2001). IGF-I or IGF-II (70RU) was coupled to a CM-5 biosensor chip (BIAcore Inc) via amine groups using standard coupling procedures (Lofas and Johnsson, 1990). Briefly, at 5 µl/min a CM5 chip was activated with 35 µl NHS (0.4 mg)/EDC (2.6 mg) and then 35 µl IGF (10 µg/ml) was coupled in 10 mM sodium acetate pH 4.5. Unreacted groups were inactivated with 35 µl 1M ethanolamine-HCl, pH 8.5. Kinetic studies with a range of hIGFBP-2 or mutant concentrations (50, 25, 12.5, 6.25 and 3.1 nM) were performed at 40 µl/min to minimize mass transport effects with 300 secs allowed for association and 900 secs for dissociation. The IGF surface was regenerated with 10 mM HCl.

Proteolysis Assay

The source of proteases for the proteolysis assays was conditioned medium of cancer cells. Cells were grown to confluence in the presence of foetal calf serum. (T84 cells are grown in DMEM: Ham's F12 (50:50 v:v) with 10% foetal bovine serum FBS; LNCaP were grown in RPMI+6% FBS; PC3 and DU145 were grown in DMEM+10% FBS, all media and FBS are from GIBCO). Cells were then washed 2×2 hours in serum free culture medium. Cells were then cultured for 3 days in serum free conditions and the medium was collected. Conditioned medium was concentrated approximately 10 fold using a centricon-10 (Millipore Corp, Mass. USA). Purified hIGFBP-2 or mutants thereof (250 ng in 2 µl) were mixed with conditioned medium for 24 hours at 37° C. to allow proteolysis. Proteins were separated on 12% tricine SDS polyacrylamide gels and transferred to nitrocellulose. Nitrocellulose filters were probed with a specific polyclonal anti-IGFBP-2 antibody (raised in our laboratory) to detect IGFBP-2 and IGFBP-2 fragments. A secondary goat anti-rabbit antibody conjugated to avidin alkaline phosphatase (Sigma) was used to detect the anti-IGFBP-2 antibody. Substrates for avidin alkaline phosphatase (nitroblue tetrazolium and 5 bromo 4 chloro 3-indolyl phosphate p-toluidine salt) were added and coloured bands indicated presence of IGFBP-2.

Matrix Binding Assay

Heparin was biotinylated using biocytin hydrazine (Pierce) using conditions recommended by the manufacturer. Following the reaction the biotinylated heparin was concentrated using a centricon-3 (Millipore Corp, Mass. USA) and was dialysed against $H_2O$. Biotinylated heparin was coupled to a streptavidin biosensor chip in 0.3M NaCl and HBS (hepes buffered saline containing surfactant, BIAcore Inc.). hIGFBP-2 and mutants at different concentrations (6.25 nM to 300 nM) were injected at 10 µl/min. Regeneration of the surface was achieved with 2M NaCl.

Proliferation of HT-29 Colorectal Cells

Cells are plated at 12,000 cells per well in 96 well plates in RPMI (GIBCO)+10% FCS (foetal calf serum), grown for 2 days, washed in serum free RPMI for 3 hours and then treated with butyrate (5 mM, Sigma) or butyrate with IGF-I at various concentrations in RPMI+5% BSA. In this experiment different amounts of IGFBP-2 or mutant IGFBP-2 were added to the butyrate+IGF-1 treated cells. Proliferation is measured using the Cell titre Glo kit from Promega. This measures ATP levels basically. IGF rescues cells from apoptosis and the binding proteins (native or mutant) inhibit the ability of IGF to rescue cells from apoptosis (sequester IGF away from the receptor).

Results and Discussion

Cloning, Expression, Purity and IGF Binding Affinities

Figure 2:
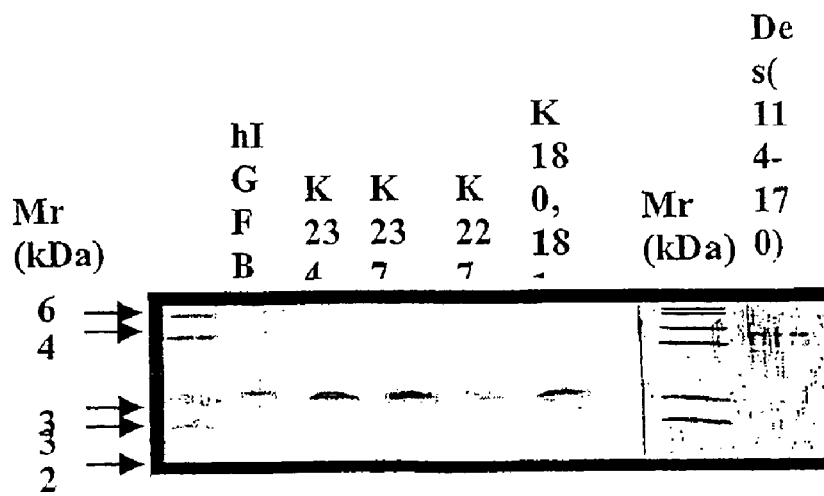
FIG. 2. Purified hIGFBP-2 and mutants were separated on a 12% tricine SDS polyacrylamide gel. Proteins were stained with Coomassie blue (except for Des(114-170)His hIGFBP-2 which was stained with sypro ruby). All mutants migrated with the expected size as estimated by comparison with molecular size standards (Novex Broad range). A minor breakdown product was detected in this particular K234AHis preparation.
Figure 3:
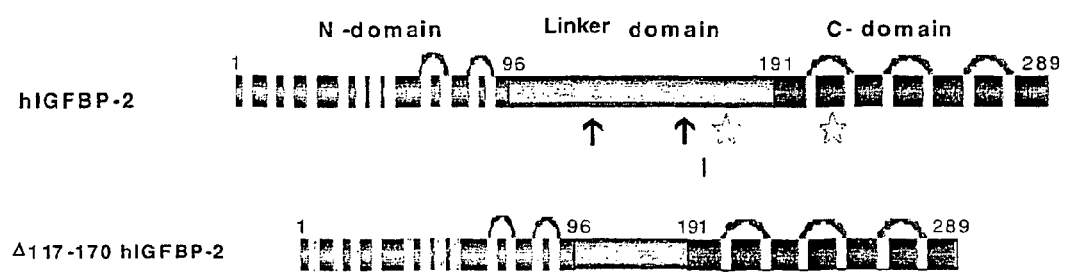
FIG. 3. Schematic of hIGFBP-2 and truncated hIGFBP-2 showing the conserved N- and C-cysteine domains connected by the linker domain. The know disulphide bonds (shown as transverse white stripes) and residue numbers are indicated above. Potential cleavage and ECM sites are also identified.

Five mutants have been designed for introduction of protease resistance or interruption of matrix binding (K180A K181AHis, K227AHis, K234AHis, K237AHis, Des(114-170)His). These were purified to homogeneity (FIG. 2) and subjected to mass spectral analysis to confirm they had the expected mass. The residues K180 and K181 are potential sites of protease cleavage (Ho, J. P. & Baxter, R. C. (1997) and are also possibly involved in matrix binding (Hodgkinson, et al (1994)). K227, K234 and K237 are residues in the analogous regions of IGFBP-3 and -5 corresponding to matrix binding motifs. The potential sites of proteolytic cleavage and matrix binding are highlighted in FIG. 3.

Figure 4:
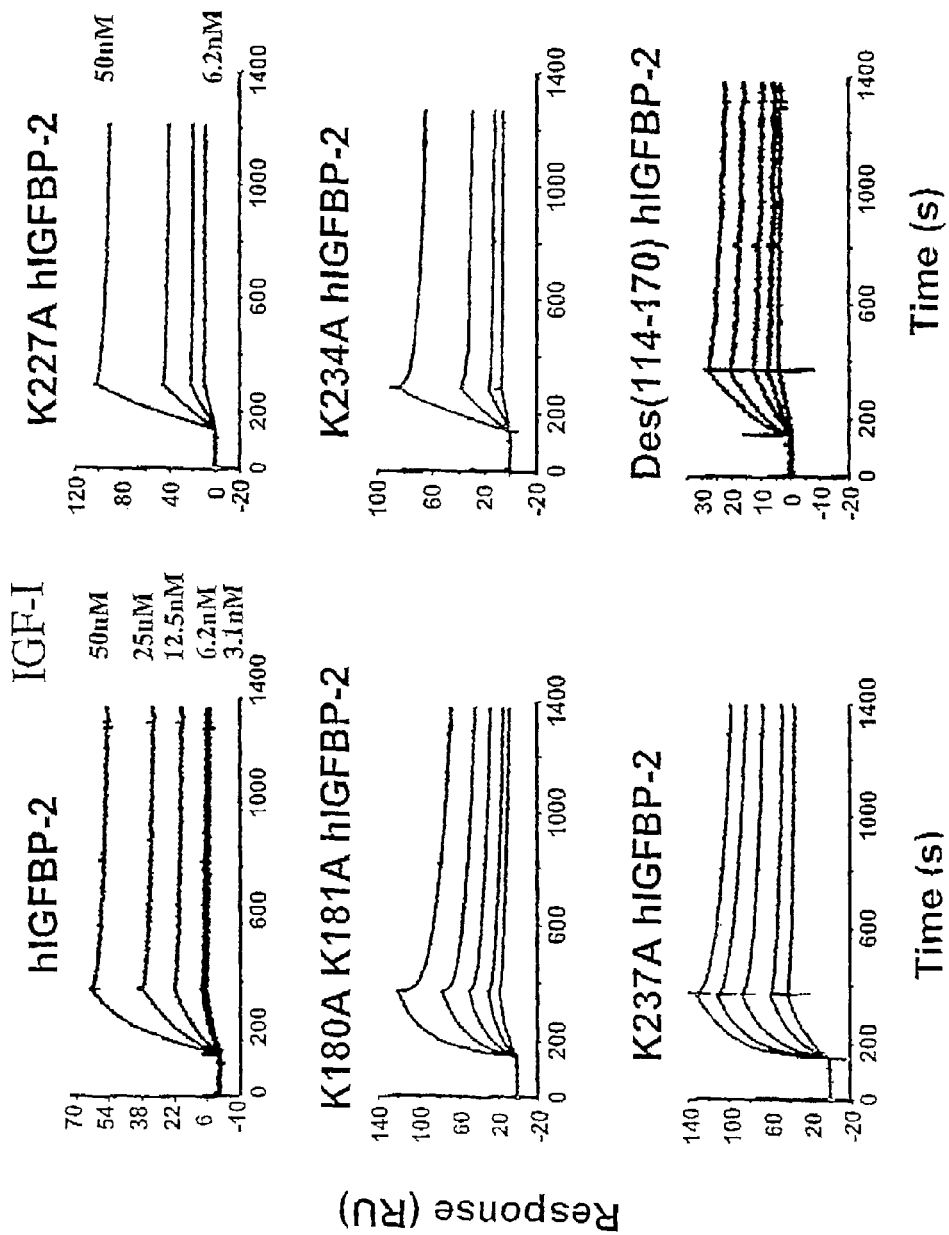
FIG. 4. BIAcore analysis of hIGFBP-2 and mutants binding to IGF-I.

The purified mutants were tested for their ability to bind IGF-I by BIAcore analysis (FIG. 4). All mutants have similar affinities to native hIGFBP-2. Mutant K237AHis has about 2 fold higher affinity for both IGF-I and IGF-II and Des(114-170)His has a 5 fold or 2 fold decrease in affinity for IGF-I and IGF-II respectively (Tables 2 and 3).

Table 2 shows the kinetic constants obtained from BIAcore analysis of hIGFBP-2 and mutant hIGFBP-2 binding to IGF-I. Data was analysed using BIAevaluation software 3.0 and fit to a Langmuir 1:1 binding model. The dissociation constant ($K_D$) was determined from the calculation of $k_d/k_a$, where $k_a$ is the association rate and $k_d$ is the dissociation rate. Relative $K_D$ is equal to $K_D$ of hIGFBP-2/$K_D$ of hIGFBP-2 mutant.

TABLE 2

| | $k_a \times 10^5$ (1/Ms) | $k_d \times 10^{-4}$ (1/s) | $k_D \times 10^{-10}$ (M) | Rel. $K_D$ |
|---|---|---|---|---|
| hIGFBP-2 | 1.8 | 1.74 | 9.67 | 1.0 |
| K180A K181A | 6.41 | 6.8 | 11.1 | 0.87 |
| K227A | 1.91 | 1.37 | 7.17 | 1.34 |
| K234A | 1.69 | 2.52 | 14.9 | 0.64 |
| K237A | 7.24 | 3.06 | 4.22 | 2.29 |
| Des(114-170) | 1.17 | 4.25 | 36.3 | 0.26 |

Table 3. Kinetic constants obtained from BIAcore analysis of hIGFBP-2 and mutant hIGFBP-2 binding to IGF-II. Data was analysed using BIAevaluation software 3.0 and fit to a Langmuir 1:1 binding model. The dissociation constant ($K_D$) was determined from the calculation of $k_d/k_a$, where $k_a$ is the association rate and $k_d$ is the dissociation rate. Relative $K_D$ is equal to $K_D$ of hIGFBP-2/$K_D$ of hIGFBP-2 mutant.

TABLE 3

| | $k_a \times 10^5$ (1/Ms) | $k_d \times 10^{-4}$ (1/s) | $k_D \times 10^{-10}$ (M) | Rel. $K_D$ |
|---|---|---|---|---|
| hIGFBP-2 | 2.38 | 1.4 | 5.89 | 1.0 |
| K180A K181A | 6.51 | 5.58 | 8.57 | 0.68 |
| K227A | 2.09 | 0.96 | 4.61 | 1.27 |
| K234A | 1.81 | 2.86 | 15.8 | 0.37 |
| K237A | 7.24 | 1.23 | 2.01 | 2.9 |
| Des(114-170) | 1.14 | 1.3 | 11.4 | 0.51 |

Protease Assays

The mutant binding proteins were tested for protease sensitivity in the assay described in materials and methods. We first analysed the truncation mutant Des(114-170)His and observed protease resistance in a number of conditioned media including T84, HT29, CaCO (all colon cancer cells) and PC3 (prostate cancer cell line). Table 4 outlines which cell lines were used, the relative amount of protease activity (qualitative from observations of gels) and which conditioned media contained proteases which are no longer able to cleave the truncation mutant.

Table 4. List of cell lines used as sources of conditioned media containing proteolytic activity. Cell lines are grouped in to cancer types. A qualitative score is given to each cell line indicating the amount of proteolytic activity evident upon incubation with hIGFBP-2 (central column). If the truncation of hIGFBP-2 (Des(114-170)His hIGFBP-2) resulted in protection against cleavage by conditioned media compared with hIGFBP-2 then this is indicated in the column on the right.

TABLE 4

|  | Proteolytic Activity | Protection |
|---|---|---|
| Prostate Cancer | | |
| LNCaP | *** | No |
| PC3 | * | Yes |
| DU145 | *** | No |
| Colon Cancer | | |
| HT29 | * | Yes |
| SW480 | ** | No |
| LIM1215 | ** | Not sure |
| CaCo | * | Yes |
| T84 | *** | Yes |
| Breast Cancer | | |
| MCF7 | * | No |

Importantly, there was a significant amount of easily detectable protease activity in the T84 cell line conditioned medium (FIG. 5A and 5B). The truncation mutant was clearly resistant to proteolysis in this medium. Proteolysis of hIGFBP-2 was also easily detected in PC3 conditioned medium and the truncation mutant was also resistant to proteolysis by this medium (FIG. 5A). In other cell lines there was less proteolytic activity making detection of protease resistance more difficult (eg LIM1215). In other cell lines the truncation mutant was clearly proteolysed (FIG. 5B).

These results highlight the fact that each cell line produces a different array of proteases. It is not known which protease is cleaving hIGFBP-2 in the T84 and PC3 media. The cleavage product in T84 medium corresponds to a C-terminal fragment of hIGFBP-2 as detected by an antibody specific for C-terminal residues. We have tested the other mutants in the T84 conditioned medium for protease resistance. As these residues lie outside the 114-170 truncation it was not surprising that none were resistant to proteolysis, suggesting that cleavage does not occur at K180, K181, K227, K234, K237.

Heparin Binding

We analyzed matrix binding using the commonly used model system of heparin binding. We analyzed heparin binding using the BIAcore. Preliminary data show that the K234A mutation reduces heparin binding 5 fold (FIG. 8) and the K180A, K181A mutation has a great effect on heparin binding. This data indicates that there are probably 2 heparin binding sites on IGFBP-2.

Table 5. Heparin binding affinities of hIGFBP-2 and K234AHis IGFBP-2 were measured by surface plasmon resonance. Data was analysed using BIA evaluation software 3.0 and fit to a Langmuir 1:1 binding model. The dissociation constant ($K_D$) was determined by the calculation of $k_d/k_a$, where $k_a$ is the association rate and $k_d$ is the dissociation rate.

TABLE 5

Heparin binding by gIGFBP-2 and mutants

|  | $K_D$ (M) |
|---|---|
| hIGFBP-2 | $1 \times 10^{-8}$ |
| K234A hIGFBP-2 | $4.82 \times 10^{-8}$ |

Proliferation of HT-29 Colorectal Cells

The assay shows that HT-29 colorectal cancer cells undergo apoptosis in 5 mM Butyrate. Addition of IGF-I rescues cells from butyrate induced apoptosis in a dose dependent manner. Additional IGFBP-2 inhibits the ability of IGF-I to rescue cells from butyrate induced apoptosis by sequestering the IGF away from the IGF receptor. The mutants Des (114-170) and Des (114-170) K180A K181A are more effective at inhibiting the action of IGF-I. This assay shows little difference between Des (114-170) and Des (114-170) K180A K181A suggesting the greatest benefit is the resistance to proteolysis conferred to the molecule by removal of protease cleavage sites. Mutation of positions K180A and K181 A could also protect from further proteolysis or inhibit interaction with the extracellular matrix. However, under the conditions of this assay it is not possible to detect a significant difference between Des (114-170) and Des (114-170) K180A K181A.

REFERENCES

Arai et al.,. *Endcrinology* 137, 4571-4575 (1996)
Arai et al., *J. Biol. Chem.* 269, 20388-20393 (1996)
Baserga, *Exp. Cell Res.* 253(1),1-6 (1999)
Braulke, *Horm. Metab. Res.* 31(2-3), 242-246 (1999)
Byun et al., *J Clin Endocrinol Metab* 85(1):373-81 (2000).
Chan et al., *Science* 279, 563-566 (1998)
Cardin. & Weintraub *Arteriosclerosis* 9, 21-32 (1989).
Carrick et al., *J. Biol. Chem.* 276, 27120-27128 (2001)
Cohen et al., *J. Clin. Endocrinol. Metab.* 79, 1410-1415 (1994)
DiGiovanni et al., *PNAS* 97, 3455-3460 (2000)
Elminger et al., *Mol. Cell. Endocrinol.* 175(1-2), 211-218 (1999)
Firth et al., *J. Biol. Chem.* 273, 2631-2638 (1998)
Forbes et al., *J. Biol. Chem.* 273, 4647-4652 (1998)
Ho & Baxter, *Clin. Endocrinol.* 46, 333-342 (1997)
Ho & Baxter *Endocrinology* 138, 3811-3818 (1997).
Hobba et al., *J. Biol. Chem.* 273:19691-19698 (1998).
Hodgkinson et al. *J. Mol. Endocrinol.* 13, 105-112 (1994);
Imai et al., *J. Clin. Invest.* 100(10), 2596-2605 (1997)
Kanety, et al. *J. Clin. Endocrinol. Metab.* 77, 229-233 (1993).
Lofas and Johnsson, *J. Chem. Soc. Chem. Commun.* 21, 1526-1528 (1990)
Menouny et al., *Endocrinology* 138, 683-690 (1997).
Michell et al., *Br. J. Cancer* 76, 60-66 (1997).
Nunn et al., *J Cell. Physiol.* 171, 196-204 (1997).
Rathjen et al., *Cell* 62(6),1105-1114 (1990)
Russo et al. *Endocrinology* 138, 4858-4867 (1997)
Sepp-Lorenzino, *Breast Cancer Res. Treat.* 47(3), 235-253 (1998)
Thrasher et al., *J. Urol.* 155, 999-1003 (1996)
Wang et al., *Nature* 372, 464-467 (1994)
Whyatt et al., *Mol. Cell. Biol.* 13, 7971-7976 (1993)
Zeslawski et al., *EMBO J.* 20, 3638-44 (2001)

The invention claimed is:

1. An altered human IGFBP-2 molecule able to bind IGF-I or IGF-II with high affinity, which differs from a human IGFBP-2 molecule by one or more of the following substitutions or deletions:
   (i) the lysine at one or more of positions 180, 181, 227, 234 and 237 of the human IGFBP-2 molecule has been replaced with a neutral or acidic amino acid; and/or
   (ii) amino acids 114-170 of the human IGFBP-2 molecule have been deleted.

2. The altered human IGFBP-2 molecule of claim 1, wherein the lysine at one or more of positions 180, 181, 227, 234 and 237 has been replaced with alanine.

3. The altered human IGFBP-2 molecule of claim 1, wherein the lysine at position 180 has been replaced with alanine.

4. The altered human IGFBP-2 molecule of claim 1, wherein the lysine at position 181 has been replaced with alanine.

5. The altered human IGFBP-2 molecule of claim 1, wherein the lysines at positions 180 and 181 have been replaced with alanines.

6. The altered human IGFBP-2 molecule of claim 5, wherein amino acids 114-170 of the human IGFBP-2 molecule have been deleted.

7. The altered human IGFBP-2 molecule of claim 1, wherein the lysine at position 234 has been replaced with alamine.

8. The altered human IGFBP-2 molecule of claim 7, wherein amino acids 114-170 of the human IGFBP-2 molecule have been deleted.

9. The altered human IGFBP-2 molecule of claim 1, wherein the lysines at positions 180, 181 and 234 have been replaced with alanines.

10. The altered human IGFBP-2 molecule of claim 9, wherein amino acids 114-170 of the human IGFBP-2 molecule have been deleted.

11. The altered human IGFBP-2 molecule of claim 1, wherein amino acids 114-170 of the human IGFBP-2 molecule have been deleted.

12. The altered human IGFBP-2 molecule of claim 1, which differs from a human IGFBP-2 molecule by the following substitutions and deletions:
   (i) the lysine at one or more of positions 180, 181, 227, 234 and 237 of the human IGFBP-2 molecule has been replaced with a neutral or acidic amino acid; and
   (ii) amino acids 114-170 of the human IGFBP-2 molecule have been deleted.

13. An isolated nucleic acid molecule encoding an altered human IGFBP-2 molecule able to bind IGF-I or IGF-II with high affinity, which differs from a human IGFBP-2 molecule by one or more of the following substitutions or deletions:
   (i) the lysine at one or more of positions 180, 181, 227, 234 and 237 of the human IGFBP-2 molecule has been replaced with a neutral or acidic amino acid; and/or
   (ii) amino acids 114-170 of the human IGFBP-2 molecule have been deleted.

14. The isolated nucleic acid molecule of claim 13, wherein the lysine at one or more of positions 180, 181, 227, 234 and 237 has been replaced with alanine.

15. The isolated nucleic acid molecule of claim 13, wherein the lysine at position 180 has been replaced with alanine.

16. The isolated nucleic acid molecule of claim 13, wherein the lysine at position 181 has been replaced with alanine.

17. The isolated nucleic acid molecule of claim 13, wherein the lysines at positions 180 and 181 have been replaced with alanines.

18. The isolated nucleic acid molecule of claim 13, wherein the lysines at positions 180 and 181 have been replaced with alanines and amino acids 114-170 of the human IGFBP-2 molecule have been deleted.

19. The isolated nucleic acid molecule of claim 13, wherein the lysine at position 234 has been replaced with alanine.

20. The isolated nucleic acid molecule of claim 13, wherein the lysine at position 234 has been replaced with alanine and amino acids 114-170 of the human IGFBP-2 molecule have been deleted.

21. The isolated nucleic acid molecule of claim 13, wherein the lysines at positions 180, 181 and 234 have been replaced with alanines.

22. The isolated nucleic acid molecule of claim 13, wherein the lysines at positions 180, 181 and 234 have been replaced with alanines and amino acids 114-170 of the human IGFBP-2 molecule have been deleted.

23. The isolated nucleic acid molecule of claim 13, wherein amino acids 114-170 of the human IGFBP-2 molecule have been deleted.

24. The isolated nucleic acid molecule of claim 13, encoding an altered human IGFBP-2 molecule able to bind IGF-I or IGF-II with high affinity, which differs from a human IGFBP-2 molecule by the following substitutions and deletions:
   (i) the lysine at one or more of positions 180, 181, 227, 234 and 237 of the human IGFBP-2 molecule has been replaced with a neutral or acidic amino acid; and
   (ii) amino acids 114-170 of the human IGFBP-2 molecule have been deleted.

* * * * *

SEQUENCE LISTING

<160> NUMBER OF SEQ ID NOS: 30

<210> SEQ ID NO 1
<211> LENGTH: 6
<212> TYPE: PRT
<213> ORGANISM: Homo sapien
<220> FEATURE:
<223> OTHER INFORMATION: Insulin-like Growth Factor Binding Protein 2

<400> SEQUENCE: 1

Pro Lys Lys Leu Arg Pro
1               5

<210> SEQ ID NO 2
<211> LENGTH: 18
<212> TYPE: PRT
<213> ORGANISM: Homo sapien
<220> FEATURE:
<223> OTHER INFORMATION: Insulin-like Growth Factor Binding Protein 2

<400> SEQUENCE: 2

Lys His Gly Leu Tyr Asn Leu Lys Gln Cys Lys Met Ser Leu Asn
1               5                   10                  15

Gly Gln Arg

<210> SEQ ID NO 3
<211> LENGTH: 23
<212> TYPE: PRT
<213> ORGANISM: Homo sapien
<220> FEATURE:
<223> OTHER INFORMATION: Insulin-like Growth Factor Binding Protein 3

<400> SEQUENCE: 3

Cys Asp Lys Lys Gly Phe Tyr Lys Lys Lys Gln Cys Arg Pro Ser
1               5                   10                  15

Lys Gly Arg Lys Arg Gly Phe Cys
                20

<210> SEQ ID NO 4
<211> LENGTH: 23
<212> TYPE: PRT
<213> ORGANISM: Homo sapien
<220> FEATURE:
<223> OTHER INFORMATION: Insulin-like Growth Factor Binding Protein 5

<400> SEQUENCE: 4

Cys Asp Arg Lys Gly Phe Tyr Lys Arg Lys Gln Cys Lys Pro Ser
1               5                   10                  15

Arg Gly Arg Lys Arg Gly Ile Cys
                20

<210> SEQ ID NO 5
<211> LENGTH: 23
<212> TYPE: PRT
<213> ORGANISM: Homo sapien
<220> FEATURE:
<223> OTHER INFORMATION: Insulin-like Growth Factor Binding Protein 2

<400> SEQUENCE: 5

Cys Asp Lys His Gly Leu Tyr Asn Leu Lys Gln Cys Lys Met Ser
1               5                   10                  15

Leu Asn Gly Gln Arg Gly Glu Cys
                20

```
<210> SEQ ID NO 6
<211> LENGTH: 23
<212> TYPE: PRT
<213> ORGANISM: Homo sapien
<220> FEATURE:
<223> OTHER INFORMATION: Insulin-like Growth Factor Binding Protein 1

<400> SEQUENCE: 6

Cys Asn Lys Asn Gly Phe Tyr His Ser Arg Gln Cys Glu Thr Ser
1               5                   10                  15

Met Asp Gly Glu Ala Gly Leu Cys
                20

<210> SEQ ID NO 7
<211> LENGTH: 23
<212> TYPE: PRT
<213> ORGANISM: Homo sapien
<220> FEATURE:
<223> OTHER INFORMATION: Insulin-like Growth Factor Binding Protein 4

<400> SEQUENCE: 7

Cys Asp Arg Asn Gly Asn Phe His Pro Lys Gln Cys His Pro Ala
1               5                   10                  15

Leu Asp Gly Gln Arg Gly Lys Cys
                20

<210> SEQ ID NO 8
<211> LENGTH: 23
<212> TYPE: PRT
<213> ORGANISM: Homo sapien
<220> FEATURE:
<223> OTHER INFORMATION: Insulin-like Growth Factor Binding Protein 6

<400> SEQUENCE: 8

Cys Asp His Arg Gly Phe Tyr Arg Lys Arg Gln Cys Arg Ser Ser
1               5                   10                  15

Gln Gly Gln Arg Arg Gly Pro Cys
                20

<210> SEQ ID NO 9
<211> LENGTH: 6
<212> TYPE: PRT
<213> ORGANISM: Homo sapien
<220> FEATURE:
<223> OTHER INFORMATION: Insulin-like Growth Factor Binding Protein 2

<400> SEQUENCE: 9

Pro Lys Lys Leu Arg Pro
1               5

<210> SEQ ID NO 10
<211> LENGTH: 6
<212> TYPE: PRT
<213> ORGANISM: Homo sapien
<220> FEATURE:
<223> OTHER INFORMATION: Insulin-like Growth Factor Binding Protein 2

<400> SEQUENCE: 10

Pro Ala Lys Leu Arg Pro
1               5

<210> SEQ ID NO 11
<211> LENGTH: 6
<212> TYPE: PRT
<213> ORGANISM: Homo sapien
<220> FEATURE:
```

-continued

<223> OTHER INFORMATION: Insulin-like Growth Factor Binding Protein 2

<400> SEQUENCE: 11

Pro Lys Ala Leu Arg Pro
1               5

<210> SEQ ID NO 12
<211> LENGTH: 6
<212> TYPE: PRT
<213> ORGANISM: Homo sapien
<220> FEATURE:
<223> OTHER INFORMATION: Insulin-like Growth Factor Binding Protein 2

<400> SEQUENCE: 12

Pro Lys Lys Leu Ala Pro
1               5

<210> SEQ ID NO 13
<211> LENGTH: 6
<212> TYPE: PRT
<213> ORGANISM: Homo sapien
<220> FEATURE:
<223> OTHER INFORMATION: Insulin-like Growth Factor Binding Protein 2

<400> SEQUENCE: 13

Pro Ala Ala Leu Ala Pro
1               5

<210> SEQ ID NO 14
<211> LENGTH: 18
<212> TYPE: PRT
<213> ORGANISM: Homo sapien
<220> FEATURE:
<223> OTHER INFORMATION: Insulin-like Growth Factor Binding Protein 2

<400> SEQUENCE: 14

Lys His Gly Leu Tyr Asn Leu Lys Gln Cys Lys Met Ser Leu Asn
1               5                   10                  15

Gly Gln Arg

<210> SEQ ID NO 15
<211> LENGTH: 18
<212> TYPE: PRT
<213> ORGANISM: Homo sapien
<220> FEATURE:
<223> OTHER INFORMATION: Insulin-like Growth Factor Binding Protein 2

<400> SEQUENCE: 15

Ala His Gly Leu Tyr Asn Leu Lys Gln Cys Lys Met Ser Leu Asn
1               5                   10                  15

Gly Gln Arg

<210> SEQ ID NO 16
<211> LENGTH: 18
<212> TYPE: PRT
<213> ORGANISM: Homo sapien
<220> FEATURE:
<223> OTHER INFORMATION: Insulin-like Growth Factor Binding Protein 2

<400> SEQUENCE: 16

Lys His Gly Leu Tyr Asn Leu Ala Gln Cys Lys Met Ser Leu Asn
1               5                   10                  15

Gly Gln Arg

```
<210> SEQ ID NO 17
<211> LENGTH: 18
<212> TYPE: PRT
<213> ORGANISM: Homo sapien
<220> FEATURE:
<223> OTHER INFORMATION: Insulin-like Growth Factor Binding Protein 2

<400> SEQUENCE: 17

Lys His Gly Leu Tyr Asn Leu Lys Gln Cys Ala Met Ser Leu Asn
1               5                  10                  15

Gly Gln Arg

<210> SEQ ID NO 18
<211> LENGTH: 18
<212> TYPE: PRT
<213> ORGANISM: Homo sapien
<220> FEATURE:
<223> OTHER INFORMATION: Insulin-like Growth Factor Binding Protein 2

<400> SEQUENCE: 18

Ala His Gly Leu Tyr Asn Leu Ala Gln Cys Ala Met Ser Leu Asn
1               5                  10                  15

Gly Gln Arg

<210> SEQ ID NO 19
<211> LENGTH: 39
<212> TYPE: DNA
<213> ORGANISM: Artificial Sequence
<220> FEATURE:
<223> OTHER INFORMATION: PCR Primer for K180A K181AHis (forward)

<400> SEQUENCE: 19
cttggcctgg aggagcctgc cgccctgcga ccacccccct                    39

<210> SEQ ID NO 20
<211> LENGTH: 39
<212> TYPE: DNA
<213> ORGANISM: Artificial Sequence
<220> FEATURE:
<223> OTHER INFORMATION: PCR Primer for K180A K181AHis (reverse)

<400> SEQUENCE: 20 aggggggtggt cgcagggcgg caggctcctc caggccaag                    39

<210> SEQ ID NO 21
<211> LENGTH: 33
<212> TYPE: DNA
<213> ORGANISM: Artificial Sequence
<220> FEATURE:
<223> OTHER INFORMATION: PCR Primer for K227AHis (forward)

<400> SEQUENCE: 21
atccccaact gtgacgccca tggcctgtac acc                           33

<210> SEQ ID NO 22
<211> LENGTH: 33
<212> TYPE: DNA
<213> ORGANISM: Artificial Sequence
<220> FEATURE:
<223> OTHER INFORMATION: PCR Primer for K227AHis (reverse)

<400> SEQUENCE: 22
ggtgtacagg ccatgggcgt cacagttggg gat                           33

<210> SEQ ID NO 23
```

```
<211> LENGTH: 33
<212> TYPE: DNA
<213> ORGANISM: Artificial Sequence
<220> FEATURE:
<223> OTHER INFORMATION: PCR Primer for K234AHis (forward)

<400> SEQUENCE: 23
ggcctgtaca acctcgccca gtgcaagatg tct                        33

<210> SEQ ID NO 24
<211> LENGTH: 33
<212> TYPE: DNA
<213> ORGANISM: Artificial Sequence
<220> FEATURE:
<223> OTHER INFORMATION: PCR Primer for K234AHis (reverse)

<400> SEQUENCE: 24
agacatcttg cactgggcga ggttgtacag gcc                        33

<210> SEQ ID NO 25
<211> LENGTH: 30
<212> TYPE: DNA
<213> ORGANISM: Artificial Sequence
<220> FEATURE:
<223> OTHER INFORMATION: PCR Primer for K237AHis (forward)

<400> SEQUENCE: 25
aacctcaaac aggccatgtc tctgaacggg                            30

<210> SEQ ID NO 26
<211> LENGTH: 33
<212> TYPE: DNA
<213> ORGANISM: Artificial Sequence
<220> FEATURE:
<223> OTHER INFORMATION: PCR Primer for K237AHis (reverse)

<400> SEQUENCE: 26
cccgttcaga gacatggcgc actgtttgag gtt                        33

<210> SEQ ID NO 27
<211> LENGTH: 36
<212> TYPE: DNA
<213> ORGANISM: Artificial Sequence
<220> FEATURE:
<223> OTHER INFORMATION: PCR Primer for Des(114-170)His (forward 1)

<400> SEQUENCE: 27
gttgcagaca atggcgccgg ccactcagaa gaagcc                     36

<210> SEQ ID NO 28
<211> LENGTH: 36
<212> TYPE: DNA
<213> ORGANISM: Artificial Sequence
<220> FEATURE:
<223> OTHER INFORMATION: PCR Primer for Des(114-170)His (reverse 1)

<400> SEQUENCE: 28
gcctccttct gagtggccgg cgccattgtc tgcaac                     36

<210> SEQ ID NO 29
<211> LENGTH: 33
<212> TYPE: DNA
<213> ORGANISM: Artificial Sequence
<220> FEATURE:
<223> OTHER INFORMATION: PCR Primer for Des(114-170)His (forward 2)

<400> SEQUENCE: 29
```

```
cggcacatgg gcaaggccgg caagcatcac ctt                                  33

<210> SEQ ID NO 30
<211> LENGTH: 33
<212> TYPE: DNA
<213> ORGANISM: Artificial Sequence
<220> FEATURE:
<223> OTHER INFORMATION: PCR Primer for Des(114-170)His (reverse 2)

<400> SEQUENCE: 30
aaggtgatgc ttgccggcct tgcccatgtg ccg                                  33
```